United States Patent [19]

DiGiacomo et al.

[11] 4,299,943

[45] Nov. 10, 1981

[54] NONAQUEOUS PREPARATION OF LAYERED OR AMORPHOUS ORGANOMETALLIC INORGANIC POLYMERS

[75] Inventors: Peter M. DiGiacomo, Mission Viejo; Martin B. Dines, Santa Ana, both of Calif.

[73] Assignee: Occidental Research Corporation, Irvine, Calif.

[21] Appl. No.: 133,859

[22] Filed: Mar. 25, 1980

[51] Int. Cl.$^3$ .................. C08G 67/00; C08G 79/00
[52] U.S. Cl. .................. 528/9; 260/429 R; 260/429.1; 260/429.2; 260/429.3; 260/435 R; 260/429.5; 528/30; 528/395; 528/222; 528/223; 528/224; 528/362; 528/374; 528/391; 528/392
[58] Field of Search .................. 528/9, 30, 395, 222, 528/223, 224, 362, 392, 374, 391; 260/429 R, 429.1, 429.2, 429.3, 429.5, 435 R

[56] References Cited

U.S. PATENT DOCUMENTS

| 3,231,347 | 2/1966 | Revukas | 44/68 |
| 3,445,492 | 5/1969 | Washburn et al. | 260/429 R |
| 3,491,133 | 1/1970 | Revukas | 260/429 R |
| 3,615,807 | 9/1971 | Yates | 106/288 B |
| 3,634,479 | 2/1971 | Ridenour | 260/429.7 |
| 3,681,265 | 8/1972 | Krueger | 528/395 |

FOREIGN PATENT DOCUMENTS

| 2614356 | 10/1977 | Fed. Rep. of Germany . | |
| 539293 | 9/1941 | United Kingdom . | |
| 1018456 | 1/1966 | United Kingdom | 528/395 |
| 1406419 | 9/1975 | United Kingdom . | |

OTHER PUBLICATIONS

Chem. Abstract 83, 70750g (1975).
Chem. Abstract 85, 13433y (1976).
Chem. Abstract 86, 155758c (1977).
Chem. Abstract 58, 1487b (1963).
Chem. Abstract 55, 11161c (1961).
Orlov & Vorankof (1965).
Dub, "Organometallic Compounds," Springer-Verlog, Berlin VIII, pp. 187-191 (1962).
Doak, et al., "Organometallic Compounds of Arsenic, Antimony and Bismuth," Wiley, Intersc., N. Y. pp. 46-49 (1970).

Primary Examiner—Wilbert J. Briggs, Sr.
Attorney, Agent, or Firm—Christie, Parker & Hale

[57] ABSTRACT

A process for producing layered organometallic polymers having organo groups covalently bonded to pentavalent metal atoms. The pentavalent metal atoms are, in turn, covalently bonded through an oxygen linkage to tetravalent metal atoms. The layered organometallic compounds are produced by reacting a silyl diester of an organo-substituted pentavalent metal acid with at least one tetravalent metal ion.

14 Claims, 8 Drawing Figures

NONAQUEOUS PREPARATION OF LAYERED OR AMORPHOUS ORGANOMETALLIC INORGANIC POLYMERS

BACKGROUND OF THE INVENTION

The present invention is directed to solid inorganic polymers having organo groups anchored to the surfaces of the polymers. The majority of the polymers formed are layered crystals which display intercalation activity.

The interface surfaces of solids, whether amorphous, crystalline, or semicrystalline, are responsive regions of chemical and physical action. In many practical chemical and physical phenomena, such as absorption, corrosion inhibition, heterogeneous catalysis, lubrication, ion exchange activity, adhesion and wetting and electrochemistry, activity occurs as a consequence of the presence of a definable solid surface.

Many inorganic solids crystallize with a layered structure and some could present sites for anchoring active groups. In this form, sheets or slabs with a thickness of from one to more than seven atomic diameters lie upon one another. With reference to FIG. 1, strong ionic or covalent bonds characterize the intrasheet structure, while relatively weak Van der Waals or hydrogen bonding occurs between the interlamellar basal surfaces in the direction perpendicular to their planes. Some of the better known examples are prototypal graphite, most clay minerals, and many metal halides and sulfides. A useful characteristic of such materials is the tendency to incorporate "guest" species between the lamella.

In this process, designated "intercalation," the incoming guest molecules, as illustrated in FIG. 2, cleave the layers apart and occupy the region between them. The layers are left virtually intact since the crystals simply swell in one dimension, i.e., perpendicular to the layers. If the tendency to intercalate is great, then the host-layered crystal can be thought of as posessing an internal "super surface" in addition to its apparent surface. In fact, this potential surface will be greater than the actual surface by a factor of the number of lamella composing the crystal. This value is typically on the order of $10^2$ to $10^4$. Although edge surface is practically insignificant compared to basal surface, it is critical in the rate of intercalation, since the inclusion process always occurs via the edges. This is because bonding within the sheets is strong and, therefore, basal penetration of the sheets is an unlikely route into the crystal.

In graphite, the function of the host is essentially passive. That is, on intercalation, the host serves as the matrix or surface with which the incoming guest molecules interact, but throughout the process and on deintercalation the guests undergo only minor perturbation.

In order for a more active process to occur during intercalation, such as selective complexation of catalytic conversion, specific groups must be present which effect such activity.

An approach in which catalytically active agents have been intercalated into graphite or clays for subsequent conversions has been described in "Advanced Materials in Catalysis," Boersma, Academic Press, N.Y. (1977), Burton et al, editors, and "Catalysis in Organic Chemistry," Pinnavia, Academic Press, N.Y. (1977), G. V. Smith, editor.

One of the few layered compounds which have potential available sites is zirconium phosphate, $Zr(O_3POH)_2$. It exists in both amorphous and crystalline forms which are known to be layered. In the layered structure, the site/site placement on the internal surfaces is about 5.3 Å, which leads to an estimated 25 Å area per site. This area can accommodate most of the functional groups desired to be attached to each site. The accepted structure, symbolized projection of a portion of a layer of this inorganic polymer and a representation of an edge view of two layers, are shown respectively in FIGS. 3, 4 and 5.

Besides the advantageous structural features of zirconium phosphate, the material is chemically and thermally stable, and nontoxic.

Quite a bit of work has been conducted on the zirconium phosphate, mainly because it has been found to be a promising inorganic cation exchanger for alkali, ammonium and actinide ions, Alberti, "Accounts of Chemistry Res." 11, 163, 1978. In addition, some limited work has been described on the reversible intercalation behavior of layered zirconium phosphate toward alcohols, acetone, dimethylformamide and amines, Yamaka and Koisuma, "Clay and Clay Minerals" 23, 477 (1975) and Michel and Weiss, "Z. Natur," 20, 1307 (1965). S. Yamaka described the reaction of this solid with ethylene oxide, which does not simply incorporate between the layers as do the other organics, but rather was found to irreversibly react with the acidic hydroxyls to form a covalent bonded product, Yamaka, "Inorg. Chem." 15, 2811, (1976). This product is composed of a bilayer of anchored ethanolic groups aimed into interlayers. The initial layer/layer repeat distance is expanded from about 7.5 Å to 15 Å, consistent with the double layer of organics present. The overall consequence of this reaction is to convert inorganic acid hydroxyls to bound organic alkanol groups.

A very recently reported effort in the field is Alberti, et al., "Journal of Inorganic Nuclear Chemistry," 40, 1113 (1978). A method similar to that of this invention for the preparation of zirconium bis(benzenephosphonate), zirconium bis(hydroxymethanephosphonate) monohydrate, and zirconium bis(monoethylphosphate) is described, with descriptions of the properties for these products.

Following the Alberti publication, a paper by Maya appeared in "Inorg. Nucl. Chem. Letters," 15, 207 (1979), describing the preparation, properties and utility as solid phases in reversed phase liquid chromatography for the compounds $Zr(O_3POC_4H_9)_2.H_2O$, $Zr(O_3POC_{12}H_{25})_2$ and $Zr(O_3POC_{14}H_{21})_2$.

An article by C. Owens et al in "Journal of Inorganic and Nuclear Chemistry," 41, 1261–1268 (1979), discusses reactions of tin halides with alkylphosphonates such as diisopropylmethylphosphonate. Owens et al disclose that reacting tin (+4) halide with an excess diisopropylmethylphosphonate (dimp) forms a complex $SnX_4.(dimp)_2$ which after sustained heating forms the complex $SnX_2.(imp)_2$ and after additional heating forms the complex $Sn(mp)_2$. Thus, the article discloses that tetravalent metal methylphosphonate can be formed by reacting a tetravalent metal salt and a methylphosphonate ester.

Owens et al in "Journal of Polymer Sciences," (B), 8, pp. 80–86 (1970) also discusses the preparation of a tetravalent metal (tin) methylphosphonate by the reaction of a metal halide and dimethylisopropyl phosphonate.

An article by Mikulski et al, in "Inorganic Chim. Acta.," 3, 523–526 (1969) discloses that a tetravalent metal halide can be reacted with diisopropylmethyl phosphonate to produce a tetravalent metal methylphosphonate. The article reports that the tetravalent metals $Sn^{+4}$, $Zr^{+4}$ and $Te^{+4}$ provide such a reaction. The product is characterized as polymeric and crystalline.

All of the compositions described herein can be useful in gas phase, liquid phase, gas liquid, reversed phase, and bulk and thin layer chromatography. The compounds can also be useful as hosts and carriers for organic molecules and especially biologically active organic molecules. They are also useful as catalysts or as supports for catalysts. For example, they can be used in an analogous fashion to the compositions which are discussed by Bailar, "Heterogenizing Homogeneous Catalysts," *Catalysis Reviews—Sci. & Eng.*, 10(1) 17–35 (1974) and Hartley and Vezey, "Supported Transition Metal Complexes as Catalysts," *Advances in Organometallic Chemistry*, 15, 189–235 (1977).

This application relates to the following copending applications, all of which are assigned to the same assignee as the present application. The entire disclosures of each of the following applications are incorporated herein by these references:

PROCESS FOR PREPARING LAYERED ORGANOPHOSPHOROUS INORGANIC POLYMERS, Ser. No. 945,971, filed Sept. 26, 1978, now U.S. Pat. No. 4,232,146 issued Nov. 4, 1980;

LAYERED CARBOXY END TERMINATED ORGANOPHOSPHOROUS INORGANIC POLYMERS, Ser. No. 952,228, filed Oct. 17, 1978, now U.S. Pat. No. 4,235,990 issued Nov. 25, 1980;

LAYERED SULFONATE END TERMINATED ORGANOPHOSPHOROUS INORGANIC POLYMERS, Ser. No. 966,197, filed Dec. 4, 1978, now U.S. Pat. No. 4,235,991 issued Nov. 25, 1980;

LAYERED ZIRCONIUM BIS (BENZENEPHOSPHONATE) INORGANIC POLYMERS, Ser. No. 7,275, filed Jan. 29, 1979;

PROCESS FOR PREPARING LAYERED ORGANOPHOSPHOROUS INORGANIC POLYMERS, Ser. No. 43,810, filed May 30, 1979;

LAYERED CYANO END TERMINATED ORGANOPHOSPHORUS INORGANIC POLYMERS, Ser. No. 54,107, filed July 2, 1979;

LAYERED ORGANOPHOSPHORUS INORGANIC POLYMERS CONTAINING MERCAPTO OR THIO GROUPS, Ser. No. 54,097, filed July 2, 1979;

LAYERED ORGANOPHOSPHORUS INORGANIC POLYMERS CONTAINING CYCLIC GROUPS, Ser. No. 60,077, filed July 24, 1979;

LAYERED ORGANOPHOSPHORUS INORGANIC POLYMERS CONTAINING OXYGEN BONDED TO CARBON, Ser. No. 60,249, filed July 24, 1979;

LAYERED ORGANOPHOSPHORUS INORGANIC POLYMERS CONTAINING MIXED FUNCTIONAL GROUPS, Ser. No. 60,250, filed July 24, 1979;

LAYERED ORGANOPHOSPHORUS INORGANIC POLYMERS CONTAINING ACYCLIC GROUPS, Ser. No. 60,079, filed July 24, 1979;

LAYERED ORGANOARSENOUS INORGANIC POLYMERS, Ser. No. 60,078, filed July 24, 1979;

LAYERED ORGANOPHOSPHORUS INORGANIC POLYMERS, Ser. No. 60,076, filed July 24, 1979;

LAYERED OR AMORPHOUS ACYCLIC ORGANOMETALLIC INORGANIC POLYMERS, Ser. No. 78,625, filed Sept. 25, 1979;

LAYERED OR AMORPHOUS CYCLIC ORGANOMETALLIC INORGANIC POLYMERS, Ser. No. 78,636, filed Sept. 25, 1979; and LAYERED ZIRCONIUM BIS (BENZENEPHOSPHONATE) INORGANIC POLYMERS, filed Jan. 4, 1980.

SUMMARY OF THE INVENTION

The inorganic polymers prepared by the process of this invention have organo groups covalently bonded to pentavalent atoms, such as phosphorus, arsenic and antimony. The pentavalent atoms are, in turn, covalently bonded by an oxygen linkage to tetravalent metal atoms. When formed in a layered crystalline state, they provide the organo groups on all of the apparent and interlamellar surfaces.

For convenience herein, the process for preparing the inorganic polymers will be described with regard to phosphorus and its selection as the pentavalent atom. However, it is to be understood that the other pentavalent atoms can be used and the description with regard to phosphorus will generally also apply analogously to the other pentavalent atoms, for example, such pentavalent atoms can be phosphorus, arsenic, antimony, vanadium, niobium and tantalum. Although phosphorus is not a metal, for the purposes herein the term "pentavalent metal" will be used to refer to these pentavalent atoms which are metals or have metal-like properties and which include phosphorus. With regard to selecting arsenic as the pentavalent metal, the general description herein of phosphorus is analogous because an arsine is analogous to a phosphine, an arsenate to a phosphate, an arsonate to a phosphonate, an arsinate to a phosphinate, an arsenic compound to a phosphorus compound, an arsenic compound to a phosphonic compound, an arsenic acid to phosphoric acid, and an arsenious acid to phosphorous acid.

The process of preparation comprises a nonaqueous, liquid media reaction in which at least one diester of an organo-substituted pentavalent metal acid is reacted with at least one tetravalent metal ion. For example, an organo-substituted phosphonate diester of the formula:

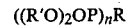

$$((R'O)_2OP)_nR$$

wherein n is 1 or 2, R is an organo group covalently coupled to the phosphorus atom, and when n is 2, R contains at least two carbon atoms and is directly or indirectly coupled to phosphorus atoms through different carbon atoms whereby the two phosphorus atoms are separated by at least two carbon atoms, and R' is a silyl group, is reacted with at least one tetravalent metal ion. R can be an organo group selected from acyclic, alicyclic, heteroacyclic, heterocyclic and aromatic groups. The molar ratio of phosphorus to the tetravalent metal ion is 2 to 1. Reaction preferably occurs in the presence of an excess of the diester compound and the metal ion is provided as a compound soluble in the liquid media.

Where only one specie of an organophosphonate diester is provided as the reactant with the tetravalent metal compound, the end product has the empirical formula $M(O_3PR)_2$.

The products formed are layered crystalline to amorphous in nature. For all products, the R groups can be directly useful or serve as intermediates for the addition or substitution of other functional groups. When the product is crystalline and n is 2, cross-linking between the interlamellar layers occurs.

The normal liquid media is a nonaqueous media comprising a non-hydroxylic organic solvent. The term "non-hydroxylic" is used herein to indicate an organic solvent not having an ordinarily replaceable hydrogen. Hydroxylic organic solvents would be organic compounds such as organic acids and alcohols. Examples of non-hydroxylic organic solvents include hydrocarbons, ethers, halogenated hydrocarbons, ketones, aldehydes, amides, esters, dimethyl sulfoxide (DMSO), dimethyl formamide (DMF) and the like.

The non-hydroxylic organic solvents are employed herein because water and hydroxylic organic solvents can interfere with the desired reaction and the organo groups designated as R in the above formula. The use of water or hydroxylic organic solvents leads to the formation of an acid intermediate which can affect the organo group. For example, if R is a cyano group, it can convert to

in the presence of dissociated hydrogen.

The non-hydroxylic organic solvent is preferably a solvent in which the diester compound of the above formula is soluble. Where the diester compound has a sufficiently low melting point, it can serve as the liquid media.

The metathesis reaction occurs at temperatures up to the boiling point of the liquid media at the pressures involved. Generally, the temperature is within the range from about −78° C. to about 400° C. and typically from ambient to about 150° C. and more preferably from ambient to about 100° C. Formation of the solid inorganic polymer is almost instantaneous, the degree of crystallinity of the product can be improved by employing a sequestering agent for the tetravalent metal ion.

DETAILED DESCRIPTION

According to the present invention there is provided inorganic polymers in layered crystalline to amorphous state formed by the liquid phase metathesis reaction of a tetravalent metal ion with a diester of an organo-substituted pentavalent metal acid, for example, at least one organo-substituted phosphonate diester having the formula:

$((R'O)_2OP)_nR$ wherein n is 1 or 2, R is an organo group covalently coupled to the phosphorus atom, and R' is a silyl group, to form a solid inorganic polymer precipitate in which the pentavalent metal (e.g., phosphorus) is linked to the tetravalent metal by oxygen and the organo group R is covalently bonded to the pentavalent metal (e.g., phosphorus) atom. The reaction occurs in a nonaqueous liquid media and preferably a non-hydroxylic organic solvent.

Figure 7:
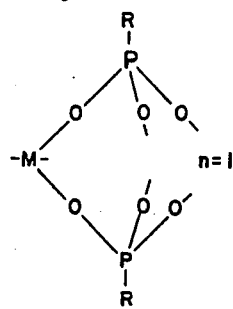
FIG. 7 shows the basic structural unit of the inorganic polymer wherein n is 1 and wherein P is phosphorus, O is oxygen, M is tetravalent metal and R is the organo group.
Figure 8:
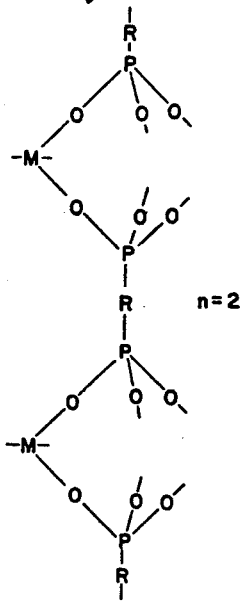
FIG. 8 shows the basic structural unit of the inorganic polymer wherein n is 2 and wherein P is a phosphorus atom, O is an oxygen atom, M is a tetravalent metal and R is the organo group.

Illustrative with phosphorus in the organophosphorus compound wherein n is 2, the end product occurs in the bis configuration. In this configuration, R must contain two or more carbon atoms, preferably from two to about twenty carbon atoms, such that at least two carbon atoms separate the phosphorus atoms. In this bis configuration, no single carbon atom is bound directly or indirectly to more than one $PO(OR')_2$ group. When n is 1, and as depicted in FIG. 7 the organo groups are pendant from phosphorus atoms. When n is 2 and, as depicted in FIG. 8, cross-linking occurs between interlamellar surfaces of the crystalline end product. Typically, the tetravalent metal ion is provided as a salt $MX_4$ soluble in the non-hydroxylic organic solvent and X is the anion(s) of the salt. Typical anions can include halides, carboxylates, alkoxides, $HSO_4^{-1}$, $SO_4^{-2}$, $O_2CCH_3^{-1}$, $NO_3^{-1}$, $O^{-2}$ and the like. Tetravalent metal ions useful herein re analogous to $Zr^{+4}$ in the process to make zirconium phosphate and phosphonate analogs and are metals with approximately the same ionic radius as $Zr^{+4}$ (0.8 Å); for example, the following tetravalent metals and respective radii (in Angstroms) can be useful:

| | | | | | | | |
|---|---|---|---|---|---|---|---|
| $Zr^{+4}$ | 0.80 | $Te^{+4}$ | 0.81 | $Pr^{+4}$ | 0.94 | $Mn^{+4}$ | 0.5 |
| $W^{+4}$ | 0.66 | $Sn^{+4}$ | 0.71 | $Pb^{+4}$ | 0.92 | $Ir^{+4}$ | 0.66 |
| $U^{+4}$ | 0.89 | $Si^{+4}$ | 0.41 | $Os^{+4}$ | 0.67 | $Hf^{+4}$ | 0.81 |
| $Ti^{+4}$ | 0.68 | $Ru^{+4}$ | 0.65 | $Nb^{+4}$ | 0.67 | $Ge^{+4}$ | 0.53 |
| $Th^{+4}$ | 0.95 | $Pu^{+4}$ | 0.86 | $Mo^{+4}$ | 0.68 | $Ce^{+4}$ | 1.01 |

The majority of the polymeric reaction products formed from the above metals are found to be layered crystalline or semicrystalline in nature and, as such, provide layered structures similar to zirconium phosphates. The remainder are amorphous polymers possessing a large quantity of available pendant groups similar to silica gel.

By the term "organo-substituted phosphonate diester," as used herein, there is meant a compound of the formula:

$$((R'O)_2OP)_nR$$

wherein n is 1 or 2, R' is a silyl group, and R is any organo group which can replace a hydroxyl of phosphoric acid and/or the hydrogen of phosphorous acid and couple to the acid by a covalent bond. Coupling to the acid can be through carbon, oxygen, silicon, sulfur, nitrogen and the like. Coupling through carbon or an oxygen-carbon group is presently preferred. The diester is then formed for the acid. Other diesters can be used wherein R' is an alkyl or aralkyl groups.

When, in the organo-substituted phosphonate diester, n is 2, the end product occurs in the bis configuration. In this configuration, R must contain two or more carbon atoms, preferably from two to about 20 carbon atoms, such that at least two carbon atoms separate the phosphorus atoms. In this bis configuration, no single carbon atom is bound directly or indirectly to more than one (PO(OR')$_2$) group. Upon reaction of the organo-substituted phosphonate diester and the tetravalent metal ion, deesterification occurs and the R' moiety is replaced with bonding to the tetravalent metal. Thus, the groups which link to the tetravalent metal have the basic structural formula:

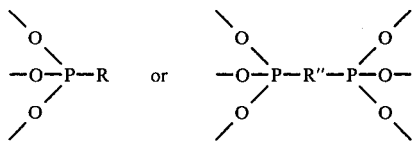

wherein R" is a bis group containing at least two carbon atoms bonded directly or indirectly to phosphorus and such that no phosphorus atoms are bonded directly or indirectly to the same carbon atom. The basic structures of the end product, inorganic polymer forms, are shown in FIGS. 7 and 8.

The product contains phosphorus to metal in a molar ratio of about 2 to 1, and the empirical formula for the product would show all groups bound to phosphorus.

As used herein, the organo group R comprises an acyclic group, heteroacyclic group, alicyclic group, aromatic group or heterocyclic group.

The term "acyclic group," as used herein, means a substituted or unsubstituted acyclic group. The term "acyclic" includes saturated and unsaturated aliphatics which can be straight chain or branched chain. The "aliphatics" include alkyl, alkenyl and alkynyl.

The term "heteroacyclic group," as used herein, means an acyclic group containing one or more heteroatoms in the chain selected from oxygen, nitrogen and sulfur. The heteroatoms can be the same or different in each chain and usually the number of heteroatoms is one, two or three.

The term "alicyclic group," as used herein, means a substituted or unsubstituted alicyclic group. The term "alicyclic" includes saturated and unsaturated cyclic aliphatics.

The term "aromatic groups," as used herein, means a substituted or unsubstituted aromatic group. The term "aromatic" includes phenyl, naphthyl, biphenyl, anthracyl and phenanthryl.

The term "heterocyclic group," as used herein, means a substituted or unsubstituted heterocyclic group. The term "heterocyclic" means an alicyclic or aromatic group containing one or more heteroatoms in the ring selected from oxygen, nitrogen and sulfur. The heteroatom can be the same or different in each ring and usually the number of heteroatoms is one, two or three.

The terms "substituted acyclic," "substituted heteroacyclic," "substituted alicyclic," "substituted aromatic" and "substituted heterocyclic," as used herein, mean an acyclic, heteroacyclic, alicyclic, aromatic or heterocyclic group substituted with one or more of the groups selected from alkyl, alkenyl, alkynyl, alkoxy, alkenyloxy, alkynyloxy, alkylthio, alkenylthio, alkynylthio, halo, oxo, hydroxy, carbonyl, carboxy, alkylcarbonyloxy, alkylcarbonyl, carboxyalkyl, thio, mercapto, sulfinyl, sulfonyl, imino, amino, cyano, nitro, hydroxyamine, nitroso, cycloalkyl, cycloalkalkyl, aryl, aralkyl, alkaryl, aryloxy, arylalkoxy, alkaryloxy, arylthio, aralkylthio, alkarylthio, arylamino, aralkylamine and alkarylamino.

Figure 1:
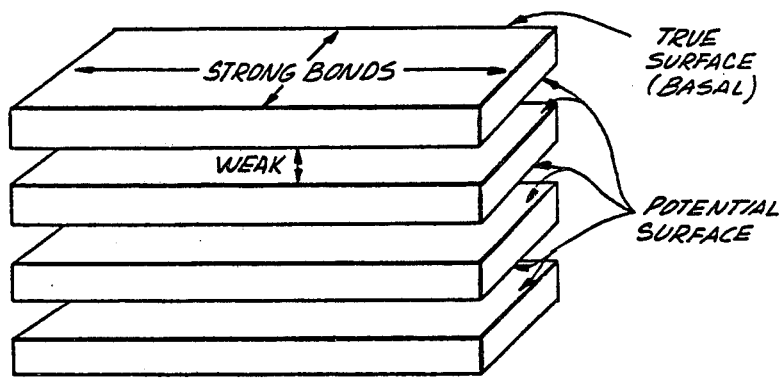
FIG. 1 illustrates a layered microcrystal. Each lamellar slab is formed of strong covalent bonds and has a thickness of about 10 atoms.
Figure 2:
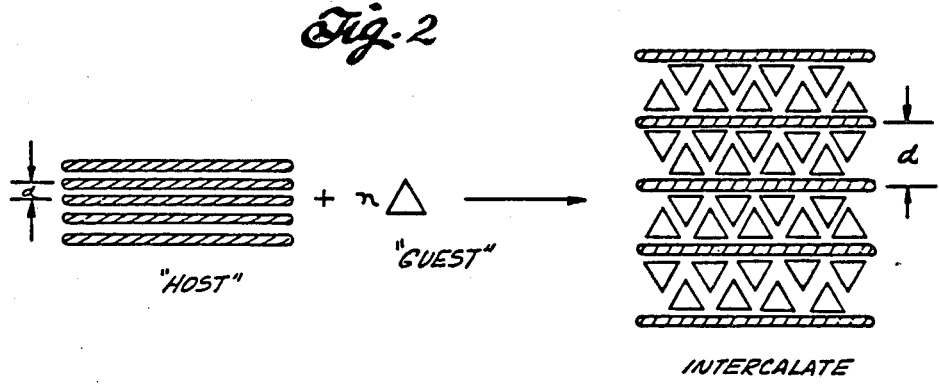
FIG. 2 illustrates intercalation where the interlayer distance is shown as "d."
Figure 3:
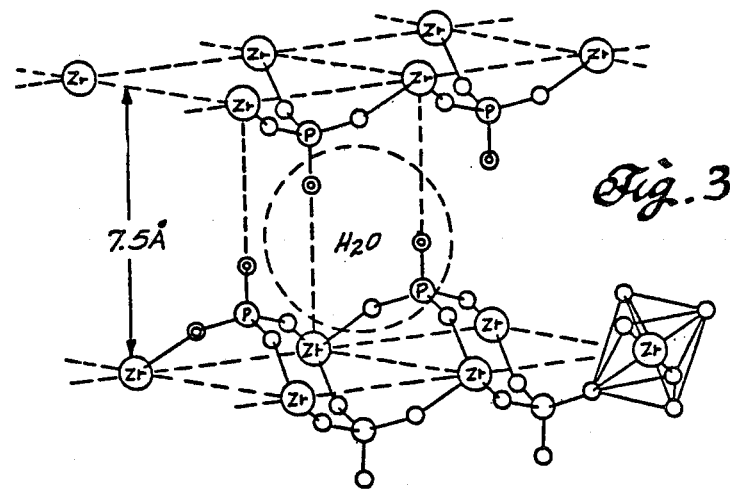
FIG. 3 illustrates the accepted structure for zirconium phosphate and spacing between layers. The dashed lines between zirconium (Zr) atoms is to establish the plane between them. In the drawing, P is phosphorus, O is oxygen and water of hydration is shown.
Figure 5:
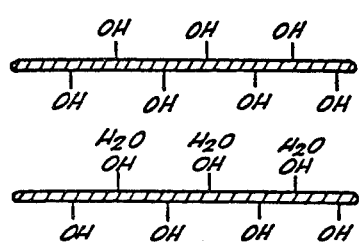
FIG. 5 is a symbolized depiction of spaced zirconium phosphate layers showing covalently bonded hydroxyl groups and water of hydration.
Figure 4:
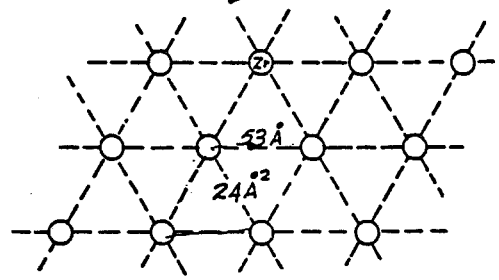
FIG. 4 illustrates a projection of zirconium plane showing accepted spacing between Zr atoms and the available linkage area.

In general, with phosphorus as the pentavalent metal, the organo group should occupy no more than about 24 Å$^2$ for proper spacing. This limitation is imposed by the basic crystal structure of zirconium phosphate. Referring to FIG. 4, a spacing of 5.3 Å is shown between zirconium atoms in the zirconium plane of a crystal. A total area of about 24 Å$^2$ is shown for the space bounded by zirconium atoms. It follows that any group anchored on each available site cannot have an area much larger than the site area and maintain the layered structure.

This limitation can be avoided through the use of a combination of larger and smaller groups, i.e., mixed components. If some of the sites are occupied by groups which have an area much less than about 24 Å$^2$, adjacent groups can be somewhat larger than 24 Å$^2$ and still maintain the layered structure of the compound.

The cross-sectional area which will be occupied by a given organo group can be estimated in advance of actual compound preparation by use of CPK space filling molecular models (Ealing Company) as follows: A model of the alkyl or aryl chain and terminal group is constructed, and it is situated on a scaled pattern of a hexagonal array with 5.3 Å site distances. The area of the group is the projection area on this plane. Some areas which have been determined by this procedure are listed in Table I.

TABLE I

| Moiety | Minimum Area (Å$^2$) | Moiety | Minimum Area (Å$^2$) |
|---|---|---|---|
| Alkyl chain | 15 | Isopropyl | 22.5 |
| Phenyl | 18 | t-butyl | 25 |
| Carboxyl | 15 | Chloromethyl | 14 |
| Sulfonate | 24 | Bromoethyl | 17 |
| Nitrile | 9 | Diphenylphosphine | 50 (approx.) |
| Morpholinomethyl | 21 | Mercaptoethyl | 13.5 |
| Trimethylamino | 25 | | |

A current method of forming tetravalent metal phosphonates is via one of the following reaction sequences:

$$M^{+4} + 2(HO)_2OPR \rightarrow M(O_3PR)_2 + 4H^+ \quad (1)$$

$$M^{+4} + 2(HO)_2OP\text{-}OR''' \rightarrow M(O_3POR''')_2 + 4H^+ \quad (2)$$

wherein R''' is an organo group. The general reaction for phosphonic acids alone is shown in reaction sequence (1) above and for monoesters of phosphoric acid alone by reaction sequence (2) above.

A disadvantage of the above reaction sequences is the acidic character of the reaction systems. The acidic character, and even the acidic moiety of the organophosphonic acid or monoester of phosphoric acid can affect substituent groups on the organic moiety R or R'''. That is, if compounds are present which have replaceable hydrogens, the availability of the replaceable hydrogens can lead to hydrolysis of hydrolysis prone substituent groups in the organic group R. Some substituent groups that may be desired in the end product can be affected (hydrolyzed) by the presence of water or some alcohols wherein the hydrogen is readily replaceable. For example, if a cyano group is present it can be hydrolyzed to

$-CNH_2$.

Thus, the nature of the inorganic layered compound desired (cyano) can be changed for some of the compounds prepared.

Substituent groups on the organic moiety can also be affected during the preparation of the organophosphonic acid reactant in the above reaction sequence. The organophosphonic acid is itself generally prepared in an acidic medium by the following reaction sequence:

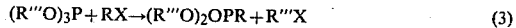
$(R'''O)_3P + RX \rightarrow (R'''O)_2OPR + R'''X$ (3)

$(R'''O)_2OPR + HCl(aq)$ or $HBr(aq) \xrightarrow{reflux} (HO)_2OPR$ (4)

Wherein X is a halogen such as Br, Cl or I. If R contains an easily hydrolyzed substituent group, the substituent group would be expected to be hydrolyzed in the strong acid hydrolyzing conditions in reaction sequence (4) above.

The present process provides a process wherein easily hydrolyzable substituent groups can be protected. The process is conducted in a nonaqueous system and in a system wherein an organophosphonic acid intermediate is not readily produced. The nonaqueous system comprises conducting the reaction in an organic solvent wherein the organic solvent is a non-hydroxylic organic solvent.

The process comprises reacting in such a nonhydroxylic organic solvent at least one silyl diester of an organo-substituted pentavalent metal acid with at least one tetravalent metal ion. With regard to phosphorus as exemplary of the pentavalent metal, the reaction can be written:

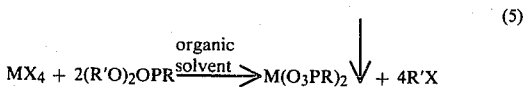
$MX_4 + 2(R'O)_2OPR \xrightarrow{\text{organic solvent}} M(O_3PR)_2 \downarrow + 4R'X$ (5)

wherein M is a tetravalent metal, X is an anionic group such as a halide, carboxylate, acetylacetonate, alkoxide, nitrate and the like, R' is a silyl group and R is an organo group desired to be anchored onto the solid phosphonate laminated compound to be formed. The reaction occurs generally at a temperature from about $-78°$ C. to about 400° C. at pressures from subatmospheric to about 1000 atmospheres in a time generally from about an almost immediate reaction to a few weeks.

The silyl diester of an organo-substituted pentavalent metal acid can be prepared in accordance with the method of Mastalerz, J. Zygmunt, P. Faforski and P. Mastalerz, *Synthesis*, p. 609 (1978). The reaction is a transesterification reaction wherein a carbon centered ester of an organophosphorus acid reacts with a silyl halide to transfer the silyl moiety to form the silyl diester and alkyl halide. The preferred silyl esters are formed from trimethylsilyl iodide. In this reaction, the carbon-centered esters can be formed in the reaction sequence (3) above. In addition, some of the carbon-centered esters are commercially available.

It has also been determined that the diester could be reacted with water to form the appropriate organo-substituted pentavalent metal acid which in turn could be used as a reactant in the reaction sequence (3) above. However, such a sequence introduces water and hydrolyzing conditions for some substituent groups which can be undesirable.

However, it is preferred herein that the diester of the organo-substituted pentavalent metal acid react directly with the tetravalent metal by the reaction sequence (5) above. In such a reaction water is not present to deesterify the diester and form the acid. The conditions of the reaction are, therefore, sufficiently mild for inhibiting any hydrolysis of substituent groups on the organo group. That is, many possible functional groups on R can be provided by this method, which functional groups can be water or acid sensitive and which were heretofore difficult to prepare.

The process for the formation of the inorganic polymers is a metathesis reaction conducted in the presence of a nonaqueous and non-hydroxylic liquid medium receptive to the tetravalent metal ion at a temperature up to the boiling point of the liquid medium, preferably from ambient to about 150° C. and, more preferably, to about 100° C. at the pressure employed.

The liquid media is a nonaqueous media comprising a non-hydroxylic organic solvent. Examples of non-hydroxylic organic solvents include hydrocarbons, ethers, halogenated hydrocarbons, ketones, aldehydes, amides, esters, dimethyl sulfoxide (DMSO), DMF and the like. The non-hydroxylic organic solvents comprise organic compounds which do not have easily replaceable hydrogens. The selection of the solvent and ease of replaceability of hydrogen on the solvent compound is relative to the hydrolyzable character of the substituent group on the R moiety.

There need only be provided a solvent for the diester of the organo-substituted pentavalent metal acid since the tetravalent ion can be dispersed as a solid in the solvent for slow release of the metal ion for reaction with the diester. If it has a sufficiently low melting point, the diester of the organo-substituted pentavalent metal acid can serve as the solvent. Typically, the liquid medium is the liquid medium in which the diester of the organo-substituted pentavalent metal acid is formed.

For complete consumption of the tetravalent metal compound, the amount of organo-substituted phosphonate diester employed should be sufficient to provide two moles of phosphorus per mole of tetravalent metal. An excess is preferred. Reaction can be instantaneous for many compounds leading to precipitation of layered crystalline, semicrystalline or amorphous solid inorganic polymer.

The amorphous phase appears as a gel similar to silica gel. The gel can be crystallized by extending the reaction conditions, i.e., reflux in the reaction medium, usually from about 5 to about 15 hours. The semicrystalline product is characterized by a rather broad X-ray powder diffraction pattern.

The presence of sequestering agents for the tetravalent metal ion slows down the reaction and also leads to more highly crystalline products. For instance, fluoride is a very strong complexing agent for zirconium ions. The slow removal of fluoride results in slow release of the tetravalent metal ion for reaction with the organo-substituted phosphonate diester resulting in an increase in crystallinity. Nitrate ion is a sequestering agent for thorium. The rate of formation of products wherein the tetravalent metal is thorium in the presence of nitrate ion is slow and the product polymer quite crystalline.

As compared to zirconium phosphate forming crystals of 1–5 microns, crystals of 100 to greater than 1000 microns in size can be prepared in accordance with the invention.

A critical property for many of the likely uses of the products is their thermal stability. This is because deficiencies in activity can be compensated for by reasonable increases in operating temperature. A standard method for thermal characterization is thermal gravimetric/differential thermal analysis (TGA/DTA). These techniques indicate changes in weight and heat flow of substances as a function of temperature. Thus, decomposition and phase changes can be monitored as temperature increases.

Zirconium phosphate itself is a stable material. Interlayer water is lost at about 100° C., and a second dehydration involving the phosphates occurs above 400° C. The practical ion-exchanging abilities are lost in this step.

The inorganic phosphorus-containing polymers are also stabilized toward thermal decomposition as compared to pure organic analogs as a result of the fixation and separating effect of the inorganic support.

For zirconium chloromethyl phosphonate, for instance, weight loss did not commence until well above 400° C. The organic fragment was half lost at about 525° C., indicating remarkable stability. Decomposition of zirconium 2-carboxyethylphosphonate begins between 300° and 400° C. The decomposition process inflection point, approximate midpoint, falls at about 400° C.

While not bound by theory, phosphates probably decompose like carboxylic esters to yield acid and unsaturates, whereas phosphonates likely form radicals by homolytic cleavage. Both nitrophenyl and cyanoethyl phosphates of zirconium decompose at about 300° C. The phenylphosphonate decomposes at about 425° C.

Besides proving the suitability of such compounds in elevated temperature applications, the TGA analysis affirmed covalent bonding to phosphorus. This is because normal intercalative interactions are reversed within 10° to 100° C. above the boiling point of the guest.

The process of this invention permits a wide variety of inorganic polymers to be formed having the characteristic of the organo group protected by the inorganic polymer structure and with subsequent exchange or substitution reactions, and the formation of other inorganic polymers. Polymers formed can be block, random and the like.

Figure 6:
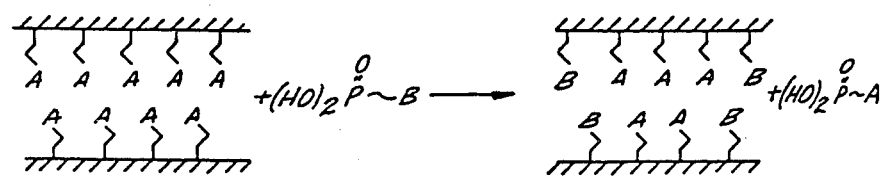
FIG. 6 illustrates an exchange reaction between anchored groups "A" and groups to be substituted for "B," and 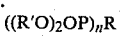 represents the portion of the organo group linking the terminal group "A" or "B" to the crystals or the organophosphorus acid compound reactant.

One such variety of inorganic polymer can be formed through exchange of one pendant group for another. The exchange reaction is described in Example 31. While not bound by theory, the present expected points of exchange are at the periphery of the crystal and are schematically illustrated in FIG. 6. Such bifunctional materials exhibit the quality of providing terminal groups for attracting species for intercalation and then interaction with the internal groups.

The reaction of bis diesters with tetravalent metal ions permits interlamellar cross-linking by a reaction such as

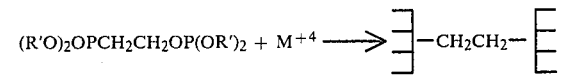

whereas in FIG. 6,

represents the interlamellar layers to which the alkyl group is anchored. As with all organo groups, for the bis configuration at least two carbon atoms are present, preferably from two to twenty atoms, and the phosphorus atoms are linked directly or indirectly to different carbon atoms. Since size of the linking group controls and fixes interlamellar spacing, there is provided effective laminar sieves of fixed spacing for application analogous to that of molecular sieves.

Ion exchange activity was established with pendant carboxylic acid groups. Prepared zirconium 2-carboxyethyl phosphonate was established to have an interlayer distance of 12.8 Å. When intercalated to form its n-hexylammonium salt, the interlayer distance increased to 27.2 Å. When sodium was taken up, layer spacing increased to 14.2 Å. X-ray and infrared data indicated the highly crystalline inorganic polymer to behave as expected for a carboxylic acid, with behavior analogous to ion exchange resins, except that both external and internal surfaces were functional, establishing them as super surface ion exchange resins. Moreover, since the inorganic polymers can be prepared as microcrystalline powders, diffusion distances are short.

As summarized in Table II, nitrile and mercapto anchored groups show the ability to take up silver and copper ions at room temperature for catalytic activity.

TABLE II

| Anchored Group | Metal Ion | Loading MMole Metal MMole Zr |
|---|---|---|
| —O~CN | 0.1 M Ag+ | 0.20 |
| ~SH | 0.1 M Ag+ | 1.0 |
| —O~CN | 0.1 M Cu++ | 0.10 |
| —O~CN | 0.1 M Cu++ 0.5 M HOAc 0.5 M NaAc | 0.10 |

~ = groups formed of carbon and hydrogen.
Ac = acetate radical

The high surface area of the crystalline products also makes them useful for sorption of impurities from aqueous and nonaqueous media.

Another utility of the products is as an additive to polymeric compositions. Similar to the high aspect ratio provided by solids such as mica which improve the stress strain properties of the polymers, the powdered inorganic polymer products can serve the same function and provide additional features. By the presence of reactive end groups on the bonded organo groups, chemical grafting to the polymer network can be achieved to increase composite crystallinity and elevating heat distortion temperature. In addition, the presence of phosphorus induces flame retardant properties, as would bound halogen.

Still other utilities include solid lubricants which behave like mica, graphite and molybdenum disulfide; solid slow release agents where intercalated materials can be slowly leached or released from the internal layers of the crystals; substance displaying electrical, optical phase or field changes with or without doping, and the like.

While nowise limiting, the following examples are illustrative of the process for preparing solid inorganic polymers in nonaqueous and non-hydroxylic systems.

In the examples, reagents were usually used as received from suppliers. The products formed are insoluble in normal solvents and do not sublime. However, the combined weight of yield data, spectroscopy, elemental analyses, TGA and powder diffraction results confirm the compositions reported with good reliability.

X-ray powder diffraction patterns were run on a Phillips diffractometer using Cuk radiation.

Thermal analyses were conducted on a Mettler instrument. Infrared spectra were obtained with a Beckman Acculab spectrophotometer.

Surface areas were determined using both dynamic flow method, on a Quantasorb instrument, and also with a vacuum static system on a Micromeritic device. Both employ a standard BET interpretation of nitrogen coverage.

EXAMPLE 1

Preparation of zirconium-3-cyanopropylphosphonate

A silyl ester of cyanopropylphosphorous acid, bis-trimethylsilyl-3-cyanopropylphosphonate, was prepared in carbon tetrachloride. The silyl ester was prepared by introducing 12 ml of $CCl_4$ to a flask. To the flask was added about 4.0 g of $(EtO)_2PO(CH_2)_3CN$. About 5.6 ml of trimethylsilyl iodide ($Me_3SiI$) was added to the flask over about 20 minutes while maintaining the temperature at about 0° C. After the $Me_3SiI$ had been introduced and following an additional 10 minutes, the temperature of the reaction mixture was allowed to raise to room temperature. Bis-trimethylsilyl-3-cyanopropylphosphonate was formed.

A 2.5 ml portion of the above prepared bistrimethylsilyl-3-cyanopropylphosphonate solution in $CCl_4$ was added dropwise 0.049 g of zirconium tetra propoxide. The reaction mixture was heated to 60° C. and filtered. The filtrate was saved. About 0.058 g of zirconium-3-cyanopropylphosphonate was formed.

The filtrate was reacted with 0.44 g of zirconium tetra propoxide. After heating, the reaction mixture was filtered. The collected solid product was washed with acetone, then ether and dried at 50° C. The dried product zirconium-3-cyanopropylphosphonate weighed 0.5 g.

EXAMPLE 2

Preparation of zirconium octadecylphosphonate

Bis-trimethylsilyloctadecylphosphonate was prepared by reacting trimethylsilyl iodide with dimethyloctadecylphosphonate according to the reaction of Mastalerz as disclosed by J. Zygmunt, P. Faforski, and P. Mastalerz, *Synthesis*, p. 609 (1978).

To a 50 ml round bottom flask was charged 1.93 g of bis-trimethylsilyloctadecylphosphonate in 5 ml of carbon tetrachloride. To the solution in the flask was added, with stirring, 0.67 g of zirconium isopropoxide followed by 3 ml of carbon tetrachloride.

The carbon tetrachloride was then removed by evaporation in a rotary evaporator. As the carbon tetrachloride evaporated, a gelatinous phase developed. The gelatinous phase developed into a solid product weighing 1.60 g. This was a yield of zirconium octadecylphosphonate of about 93%.

Thermal analysis indicated a 65% weight decrease at about 480° C. This weight loss corresponds to a theoretical weight decrease of 67% for loss of the $C_{18}H_{37}$ fragment.

The zirconium octadecylphosphonate has utility as a host for slow release of biochemical compounds.

EXAMPLE 3

Preparation of zirconium-4-carboethoxybutylphosphonate

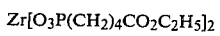

$Zr[O_3P(CH_2)_4CO_2C_2H_5]_2$

Bis-trimethylsilylcarboethoxybutylphosphonate was prepared by reacting 9.46 g $(EtO)_2OP(CH_2)_4COOEt$, (Et represents an ethyl group) with 15.71 g trimethylsilyl iodide in 50 ml of carbon tetrachloride with stirring at 0° C. The reaction flask was purged with nitrogen. The trimethylsilyl iodide was added quickly to the reaction mixture through an addition funnel. The addition funnel was rinsed with 20 ml carbon tetrachloride and added to the flask. The reaction mixture was then stirred for about 20 minutes.

The carbon tetrachloride was evaporated in a rotary evaporator. The product remaining was bis-trimethylsilylcarboethoxybutylphosphonate.

To a reaction flask under an inert atmosphere was added 3.13 g of bis-trimethylsilyl-4-carboethoxybutylphosphonate. To the flask was slowly added 1.44 g of zirconium propoxide. After the first few drops were added, a gelatinous product was formed. Agitation was continued during the remainder of the addition.

The product, zirconium-4-carboethoxybutylphosphonate, was collected on a fine fritted filter funnel and washed with acetone followed by ethyl ether and air dried. The solid product weighed 1.99 g.

The infrared spectrum of the product showed a strong ester carbonyl absorption band at about 1730 $cm^{-1}$. The X-ray powder diffraction pattern indicated a moderately crystalline material with an interlayer spacing of 18.4 Å.

EXAMPLE 4

Preparation of zirconium-2-(4'-pyridyl)phosphonate

To a chloroform solution of 29 g diethyl-2-(4'-pyridyl)ethylphosphonate was added dropwise, 80 g trimethylsilyliodide. The reaction temperature was kept cold with an ice bath. The reaction mixture was maintained under an inert atmosphere. After 2 hours, the reaction mixture was allowed to warm to room temperature.

To the reaction mixture was added 35.7 g of zirconium propoxide dropwise. A yellow solid was formed as the reaction proceeded. The solid produced was isolated and washed with ethyl ether.

The solid product recovered was yellow. It was analyzed by infrared spectroscopy. Absorption bands at 1610 (should be at 1580), 1520, and 1480 $cm^{-1}$ indicate a pyridyl group and a strong band at about 1100 cm$^{-1}$ indicates the phosphonate group. Elemental analysis indicates that the product was about 45% pure with the impurities being inorganic impurities.

The zirconium-2-(4'-pyridyl)phosphonate can be used as a ligating agent, such as a palladium host.

EXAMPLE 5

Preparation of

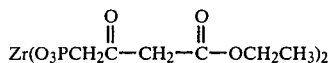

To a reaction flask was added 1.646 g of ethyl 4-chloro-aceto-acetate in 20 ml of acetone. Added to the flask was 1.80 g of NaI dissolved in 12 ml of acetone. The resulting slurry was stirred. A few grains of sodium thiosulfate was added to complex with the iodine released.

A yellow solution formed upon mixing the two solutions in which formed a white solid, NaCl. The solid phase formed took up most of the solution volume. Produced was

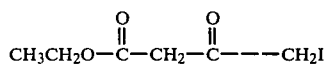

in an amount of 3.164 g.

In a separate reaction flask was added 1.50 g of the iodo ketone product produced above. To the reaction flask was then added 2.00 g of triethyl phosphite. Upon mixing, a bubbling occurred and the reaction mixture changed from dark red to an iodine color. The mixture was heated to 50° C. for about 25 minutes. An orange gel appeared which, after separation, weighed 4.731 g which was

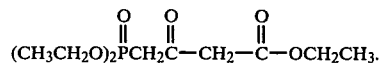

Upon NMR analysis there was shown to be 19 hydrogens. Upon gas chromatographic analysis, two peaks were predominant of equal intensity.

The

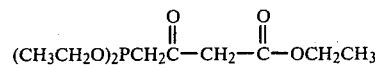

was reacted with trimethyl silyl iodide to produce

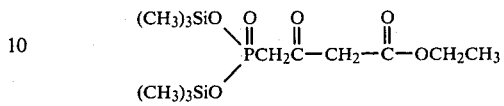

Into a three-necked flask was placed 1.164 g of Zr(OC$_3$H$_7$)$_4$ dissolved in 10.0 ml of carbon tetrachloride and 2.300 g of the silated product produced above dissolved in 10 ml carbon tetrachloride. A precipitate appeared almost immediately. The reaction mixture appeared to thicken. An additional 20 ml of carbon-tetrachloride for a total of 40 ml CCl$_4$. The reaction mixture was allowed to react over the weekend.

The reaction mixture was filtered to collect the precipitate that had formed. The recovered precipitate was washed with CCl$_4$ followed by ether. Repeated ether washes were performed until the solid was a cream white color. The recovered solid weighed 1.343 g.

An infrared analysis evidenced a C=O stretching was present.

EXAMPLE 6

Preparation of titanium phenylphosphonate

Bis-trimethylsilylphenylphosphonate is prepared by reacting diethylphenyl phosphonate and trimethylsilyl iodide according to the reaction of Mastalerz.

To the resulting mixture is added titanium tetrachloride. The mixture is heated to about 100° C. for about an hour during which time a gel appears. The gel hardens to a solid with additional heating and time.

The solid is recovered and washed with acetone and ethyl ether then suction dried. The solid product is white in color with a bluish tinge.

EXAMPLES 7-30

Using the method outlined in Example 1, the following compounds are prepared:

| Ex. | | |
|---|---|---|
| 7. | M(O$_3$P—(CH$_2$)$_n$—PR$_2$)$_2$ | M = Ti$^{+4}$, Zr$^{+4}$, Hf$^{+4}$ U$^{+4}$, Th$^{+4}$, Pb$^{+4}$; n = 1-10; R = —CH$_3$, —C$_2$H$_5$, —C$_6$H$_5$. |
| 8. | M(O$_3$P—(CH$_2$)$_n$—CH$_3$)$_2$ | M as above and n = 1-22. |
| 9. | M(O$_3$P—(CH$_2$)$_n$—OP(OR)$_2$)$_2$ | M, n, R as above. |
| 10. | M(O$_3$P—(CH$_2$)$_n$—$^+$N(CH$_3$)$_3$X$^-$)$_2$ | M, n as above; X = halide, sulfate nitrate, phosphate acetate. |
| 11. | M(O$_3$P—C$_6$H$_4$X)$_2$ | M and X as above. |
| 12. | M(O$_3$P—CH$_2$—C$_6$H$_4$X)$_2$ | M and X as above. |
| 13. | M(O$_3$P—(CH$_2$)$_n$—NH—CS$_2$H)$_2$ | M, n as above. |
| 14. | M(O$_3$P(CH$_2$)$_n$—$\overset{+}{N}$(CH$_2$CO$_2$H)$_2$ | M, n as above. |
| 15. | M(O$_3$P(CH$_2$)$_n$—$\overset{+}{N}$H$_2$—(CH$_2$)$_3$SO$_3^-$)$_2$ | M, n as above. |
| 16. | M(O$_3$P—(CH$_2$)$_n$—NC)$_2$ | M, n as above. |
| 17. | M(O$_3$P—(CH$_2$)$_n$—C≡CH)$_2$ | M, n as above. |
| 18. | M(O$_3$P—O—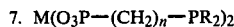)$_2$ | M as above. |

| Ex. | | |
|---|---|---|
| 19. | $M(O_3P-(CH_2)_n$ 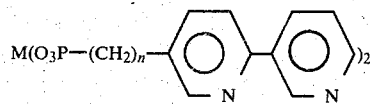$)_2$ | M, n as above. |
| 20. | $M(O_3P-(CH_2)_n-SR)_2$ | M, n as above; $R = -CH_3, -C_2H_5$. |
| 21. | $(M(O_3P-(CH_2)_n$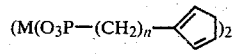$)_2$ | M, n as above. |
| 22. | $(M(O_3P-(CH_2)_n\overset{O}{\overset{\|}{C}}H)_2$ | M, n as above. |
| 23. | $(M(O_3P-(CH_2)_n$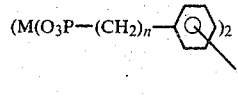$)_2$ | M, n as above. |
| 24. | $M(O_3P-(CH_2)_n$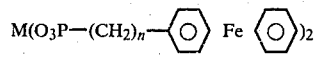$Fe$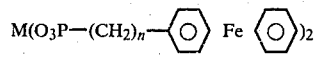$)_2$ | M, n as above. |
| 25. | $M(O_3P-(CH_2)_n-C(SH)=CH(SH))_2$ | M, n as above. |
| 26. | $M(O_3P-(CH_2)_n$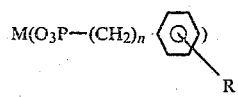$)$ | M, n as above, $R = -CH_3, -C_2H_5,$ $-CH(CH_3)_2$ or $-C(CH_3)_3$ as in 1. |
| 27. | $M(O_3P-(CH_2)_nOPR_2)_2$ | M, n and R as in 1. |
| 28. | $M(O_3P-(CH_2)_n-Br_2)_2$ | M, n and R as in 1, or R = H. |
| 29. | $M(O_3P-(CF_2)_n-SO_3H)_2$ | M, n as above. |
| 30. | Compounds above in which the $P-(CH_2)_n$ linkage is replaced by a $P-O-(CH_2)_n$ link. | |

EXAMPLE 31

Solid zirconium 2-bromoethyl phosphonate was slurried in an aqueous solution of 2-carboxyethyl phosphonic acid. A trace (1% mol) of HF was added and the mixture refluxed overnight. The infrared spectrum of the solid after this period definitely showed the presence of the carboxylic acid carbonyl band at 1710 $cm^{-1}$. The X-ray powder pattern of the exchanged product was virtually identical to the starting material. This was likely due to the fact that zirconium 2-bromoethyl phosphonate has an interlayer spacing of 13.0 A and the 2-carboxy analog 12.8 A. Based on stoichiometry, about 5 to 10 percent of the sites were exchanged. This being more than the apparent surface site, interlamellar exchange took place.

COMPARATIVE EXAMPLE 32

An alternative method of preparation involves conversion of dialkyl phosphonate esters to bis(trimethylsilyl) esters, followed by hydrolysis to the phosphonic acid using an equivalent amount of water and then reacting with tetravalent metal ion.

In an experiment to demonstrate this method, 4.0 g of diethyl-3-cyanopropylphosphonate in 12 ml of carbon tetrachloride, was treated with 5.6 ml of trimethylsilyl iodide. This was cooled to 0° C. and stirred for ten minutes, and allowed to warm to room temperature, forming bis(trimethylsilyl)-3-cyanopropylphosphonate.

A 10 ml portion of the reaction mixture was treated with 2.5 ml of deionized water, forming two phases. The upper (aqueous) phase contained 3-cyanopropylphosphonic acid, and was separated. The aqueous phase was diluted with about 20 ml of deionized water, and 4.8 g of zirconiumoxychloride octahydrate in 10 ml of water was added, forming a white precipitate.

The solid product, zirconium bis(3-cyanopropyl) phosphonate, was isolated by filtration, was successively washed with water, acetone and ethyl ether, then dried at about 35° C. The yield was 1.8 g. The infrared absorption spectrum shows the presence of a cyano group by a sharp absorption at 2240 $cm^{-1}$.

What is claimed is:

1. A process for the production of a solid polymeric compound having basic structural units of the formula:

$$M(O_3ZO_xR)_n$$

wherein M is at least one tetravalent metal, Z is a pentavalent metal and R is at least one organo group covalently coupled to the pentavalent metal and selected from the group consisting of acyclic, alicyclic, heteroacyclic, heterocyclic and aromatic groups, X is 0 or 1 and n is 2 provided that n is 1 when R is terminated with a tri- or tetra-oxy pentavalent metal, the process comprising reacting in a non-hydroxylic organic solvent at least one diester of an organo-substituted pentavalent metal acid of the formula:

$$((R'O)_2OZ)_nR$$

wherein n is 1 or 2, R' is a silyl group and Z and R are defined as above, with at least one tetravalent metal ion to precipitate the solid compound.

2. A process as recited in claim 1 wherein the reaction is conducted at a temperature between about −78° C. to about 400° C.

3. A process as recited in claim 1 wherein the non-hydroxylic organic solvent is selected from the group consisting of ethers, hydrocarbons, halogenated hydrocarbons, ketones, aldehydes, amides, esters, dimethylsulfoxide and dimethyl formamide.

4. A process as recited in claim 1 wherein the tetravalent metal ion is provided as a salt of the tetravametal ion which is soluble in the non-hydroxylic organic solvent.

5. A process as recited in claim 4 wherein the anion of the tetravalent metal salt is selected from the group consisting of halides, carboxylates, acetylacetamates, alkoxides and nitrates.

6. A process as recited in claim 1 wherein the non-hydroxylic solvent comprises the diester of an organo-substituted pentavalent metal acid.

7. A process as recited in claim 1 wherein the pentavalent metal is selected from the group consisting of phosphorus, arsenic, antimony, vanadium, niobium and tantalum.

8. A process as recited in claim 1 wherein the tetravalent metal ion is selected from the group consisting of titanium, zirconium, molybdenum, tin, cerium, hafnium, lead, thorium and uranium.

9. A process as recited in claim 1 wherein R' comprises:

$(CH_3)_3Si-$.

10. A process as recited in claim 1 in which R is an acyclic group having from about 3 to about 22 carbon atoms, which can be substituted with one or more of the constituents selected from halo, carboxy, aldo, keto, phenyl, cyano, mercapto, nitro, thio, amino, oxy, sulfo, hydroxy, cyclo having from 3 to about 6 carbon atoms, phosphonate, phosphate, phosphine, phosphinoxo, oxyphenyl, heterocyclics having from about 2 to about 11 carbon atoms and having at least one nitrogen, oxygen or sulfur atom in the heterocyclic ring, or phenyl which is substituted with one or more of the above constituents.

11. A process as recited in claim 1 in which R is an alicyclic group having from about 3 to about 6 carbon atoms selected from the group consisting of a saturated or unsaturated cyclic aliphatic group, either unsubstituted or substituted with one or more of the groups selected from alkyl, alkenyl, alkynyl, alkoxy, alkenyloxy, alkynyloxy, alkylthio, alkenylthio, alkynylthio, halo, oxo, hydroxy, carbonyl, carboxy, alkylcarbonyloxy, alkylcarbonyl, carboxyalkyl, thio, mercapto, sulfinyl, sulfonyl, imino, amino, cyano, nitro, hydroxyamino, nitroso, aryl, aralkyl, alkaryl, aryloxy, arylalkoxy, alkaryloxy, arylthio, aralkylthio, alkarylthio, arylamino, aralkylamino, and alkarylamino groups.

12. A process as recited in claim 1 in which R is a heterocyclic group having from about 2 to about 11 carbon atoms and selected from the group consisting of an alicyclic or aromatic group containing one or more of the heteroatoms oxygen, nitrogen or sulfur in the ring, which can be substituted with one or more of the groups selected from alkyl, alkenyl, alkynyl, alkoxy, alkenyloxy, alkynyloxy, alkylthio, alkenylthio, alkynylthio, halo, hydroxy, carbonyl, carboxy, alkylcarbonyloxy, alkylcarbonyl, carboxyalkyl, thio, mercapto, sulfinyl, sulfonyl, imino, amino, cyano, nitro, hydroxyamino, nitroso, aryl, aralkyl, alkaryl, aryloxy, arylalkoxy, alkaryloxy, arylthio, aralkylthio, alkarylthio, arylamino, aralkylamino, and alkarylamino groups.

13. A process as recited in claim 1 in which R is a heteroacyclic group having from about 2 to about 22 carbon atoms selected from the group consisting of a branched or straight chain, saturated or unsaturated acyclic group containing one or more of the heteroatoms oxygen, nitrogen or sulfur in the chain, which can be substituted with one or more of the groups selected from halo, hydroxy, carbonyl, mercapto, sulfinyl, sulfonyl, imino, amino, cyano, nitro, hydroxyamino, nitroso, aryl, aryloxy, arylthio and arylamino groups.

14. A process as recited in claim 1 in which R is an aromatic group, the aromatic group comprising biphenyl, anthracyl, phenanthryl or having the following formula:

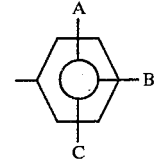

in which A is H, F, Cl, Br, I, $NO_2$, $SO_3H$, OH or COOH, B is H, F, Cl, Br, I, $NO_2$, $SO_3H$, OH or COOH, C is F, Cl, Br, I, $NO_2$ or COOH or A and B together are $-CH=CH-CH=CH-$.

* * * * *